United States Patent [19]

Schall, Jr.

[11] 4,152,411
[45] May 1, 1979

[54] HIGH SPECIFIC ACTIVITY LABELED SUBSTANCES

[75] Inventor: Roy F. Schall, Jr., Glendora, Calif.

[73] Assignee: Akzona Incorporated, Asheville, N.C.

[21] Appl. No.: 819,546

[22] Filed: Jul. 27, 1977

[51] Int. Cl.$^2$ ............... A61K 27/04; G01N 23/00
[52] U.S. Cl. ............................ 424/1; 23/230 B; 23/230.3; 424/12
[58] Field of Search .............. 424/1, 12; 23/230 B, 23/DIG. 16, DIG. 21

[56] References Cited
U.S. PATENT DOCUMENTS

| | | | |
|---|---|---|---|
| 3,592,888 | 1/1968 | Wolf | 424/1 |
| 3,843,775 | 10/1974 | Wolf | 424/1 |
| 3,880,934 | 4/1975 | Rammler | 424/12 |

*Primary Examiner*—Leland A. Sebastian
*Attorney, Agent, or Firm*—Robert H. Falk; Charles A. Wendel; Francis W. Young

[57] ABSTRACT

A new diagnostic labeled spine tool is disclosed for use in immunoassay techniques, e.g., determination of a component of the antigen-antibody reaction. The new tool is a labeled-spine material product of the formula

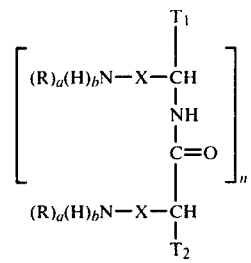

where R is an organic group labeled with a radioisotope, fluorescent group, lysis-initiating compound, enzyme, or other suitable marker material; $T_1$ and $T_2$ are any of —$CH_3$,

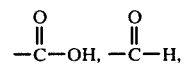

—$CH_2OH$, —$CH_2SH$, and —$NH_2$;

X is selected from the group consisting of $(CH_2)_m$, where m is an integer from 0 to about 10, phenylene, hydroxyl-substituted phenylene, halogen-substituted phenylene, alkyl substituted phenylene or aminated phenylene groups;

a is 0, 1 or 2;

b is 2-a, with the proviso that there be at least two R groups in the product; and n is a number from 1 to about 100,000

The new tool provides higher specific activity for labeled substances thus facilitating determination of the desired compound. Preferably R is an enzyme, a is one, and X is of the formula $(CH_2)_m$, where m is from 2 to 5.

7 Claims, No Drawings

HIGH SPECIFIC ACTIVITY LABELED SUBSTANCES

BACKGROUND TO THE INVENTION

1. Field of the Invention

The invention relates to the field of immunoassay techniques for the identification and quantification of antigens, haptens, and antibodies and other compounds and substances of interest in biological fluids, and to the subfields of enzyme-immunoassay techniques and general methods for increasing specific activity of marker units.

2. Description of Prior Art

There are several types of test systems useful for the detection and measurement in serum or other media of biologically important or interesting compounds or substances:

1. Radioassay techniques (RIA)
   a. Competitive protein binding assays
   b. Radioimmunoassay
   c. Immunoradiometric assays
   d. Sandwich or 2-site immunoradiometric assays
2. Fluoroimmunoassays (FIA)
3. Enzyme immunoassay (EIA)
4. Lysis-initiating immunoassays (LIA)
5. Latex-particle agglutination (LPA)
6. Charcoal-particle agglutination (CPA)
7. Hemagglutination and Hemagglutination Inhibition Assays (HA)
8. Complement Fixation (CF)
9. Counter-electrophoresis, Immunoelectrophoresis (CEP)
10. Radial Immunodiffusion and Double diffusion (RID)
11. Viroimmunoassay (VIA); and
12. Spin immunoassay (SIA) among others.

Most of these tests are limited by one or more of the following limitations: (1) lack of sensitivity, (2) complexity of the test procedure, (3) instability of reagents, (4) hazardous reagents, (5) impure reagents, and (6) expensive equipment required.

Of the limitations cited above, the most serious is lack of adequate sensitivity. In general three levels of sensitivity are recognizable. Low sensitivity techniques, where materials detected and measured exist in microgram/milliliter quantities, include RID, CF, CEP, CPA, and LPA. Intermediate sensitivity techniques, where microgram/milliliter to nanogram/milliliter quantities of materials may be measured, include HA, CF, FIA, SIA, VIA, and EIA. Until now only RIA was able to measure with ultrasensitivity the picogram/milliliter to femtogram/milliliter region.

Many of the techniques listed required that some form of physical or chemically identifiable label be attached to reagents in the assay system in order that the result of a test can be detected, RIA, FIA, EIA, LIA, VIA, and SIA all fall into this category. Radioactivity, fluorescent moieties, enzymes, complement, viruses, and electron-spin labels are used respectively to generate some form of end-point signal. The sensitivity with which these labels can be detected directly and fundamentally affects the useful ranges of the test systems using them. For a review of the development and evaluation of immunological methods and their uses as diagnostic laboratory tools, reference is made to "Immunology as a Laboratory Tool" by Frans Peeton, in American Journal of Medical Technology, 37, #12, 455–469 (1971).

The sensitivity with which a labelling moiety can be measured depends upon the nature of the signal it generates, the ability to detect that signal, and upon the intensity of signal available per unit amount of marker molecule—its specific activity. With radioactive labels, heretofore the most popular label in use, the signal is decay radiation. Because of the penetrating properties of the emissions generated, radioactive decay can be detected easily. Modern counting equipment very efficiently measures the radioactive emissions from even a small amount of radioactivity. Finally, there is a range of specific activities offered by isotopes currently used for tagging.

Table I

Some Properties of Radioactive Isotopes Widely Used for Tagging Biological Materials

| Isotope | Specific Activity of Pure Isotope (Curies/Mole) | Half Life |
|---|---|---|
| $^{14}C$ | $6.25 \times 10^1$ | 5720 years |
| $^{3}H$ | $2.91 \times 10^4$ | 12.3 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

The specific activity of a radioactively tagged compound depends upon several factors: the half life of the isotope used for labeling, the isotopic purity of the label, and finally how much of the label has been incorporated into the compound.

Radioactive isotopes of many elements are available for taggingbiological materials. Each isotope has its own unique half life. Thus a wide selection of specific activities for tagging are available merely byselecting an optimum radioisotope. Table I lists several commonly used radioisotopes, their specific activities and half lines. In general for use in immunoassays, the higher the specific activity of a radiolabeled compound, the better.

In a similar way enzymes may be characterized by the rate of catalytic effects on their respective substrates, their isoenzymatic purities, and the degree of incorporation of enzyme into labeled compound. In general however, if the enzyme is specified, the variables which can be adjusted to improve specific enzymatic activity are limited to the degree of incorporation into the tagged compound.

In contrast with radioiodine where several isotopes are available, selected isoenzymes of an enzyme family are often not available or are prohibitively expensive. The enzymes are specific to unique or narrowly restricted groups of substrates and thus substrate turn over rates, the rate at which enzyme catalyzes a substrate reaction, are fixed. Finally examples have been found which indicate that inclusion of several enzyme moieties per labeled molecule frequently destroys the characteristics for which that molecule was selected.

The thrust of this new invention is a way of incorporating two or more enzyme moieties (but not merely limited to enzymes) into a label without destroying the properties for which the labeled compound was originally selected. This is accomplished by introducing a novel linking moiety to the labeled compound. Attached to the linking moiety are the labeling enzymes in amounts that would normally alter the properties of the labeled compound if they were directly attached. The compound labeled in this way has greatly elevated specific enzymatic properties without losing the properties for which it was selected.

Up to the present time, the radioimmunoassay (RIA) method in its various forms has been the most sensitive system available. The RIA method, unfortunately, has several disadvantages, including the requirement of special equipment, trained staff, the need for extra safety measures to protect against harmful radiation, special licensing, and the regular disappearance of labeled compound by radioactive decay. The possibility of replacing the radioactive label with an enzyme label was proposed in 1968 in an article by L. E. M. Miles and C. N. Hales, entitled "Labelled Antibodies and Immunological Assay Systems," Lancet, II, 492 (1968) and Nature 219, 168 (1968), but no procedural details were provided, the article failing to offer more than the general idea, leaving it to future workers to determine the basic steps and to perform the extensive experimentation needed to establish a practical operative enzymatic immunoassay method.

While the present invention can be employed for RIA methods, it grew out of the application of EIA methods to the measurement of antigens, haptens, and antibodies to overcome the classical problems of RIA.

The pioneering work on enzyme-immunoassay (EIA) methodology (wherein one component in the immunochemical reaction is preferably insolubilized) was performed by Schuurs and coworkers, and is disclosed in a series of their U.S. Pat. Nos. 3,654,090, 3,791,932, 3,850,752, 3,839,153, 3,879,262, 4,016,043, and Re 29,169. Another line of EIA methodology is the so-called "homogenous" form which does not require separation of free and bound enzyme label, because the assay depends on the inhibition or activation of the enzyme label by antibody binding. See G. Brian Wisdom, "Enzyme-Immunoassay," Clinical Chemistry 22/8, 1243 (1976). Unfortunately, while RIA had the disadvantages of special equipment, special licenses, and highly-trained staff, its inherent sensitivity down to $10^{-12}$ gram antigen was highly desirable, especially for the detection and determination of antibodies and antigens relating to the diseases of hepatitis-B surface antigen (hereinafter referred to simply as hepatitis), rubella, and Neisseria gonorrhoeae (hereinafter referred to simply as gonorrhoea) which are difficult, if not impossible, to measure by homogenous EIA techniques because impractically large volumes of sample are required, and difficult by normal insolubilized forms of EIA techniques.

In an effort to raise the sensitivity of various marker techniques, several investigators have attempted to increase the number of markers per hapten, antigen, or antibody. With respect to FIA, John Axel Sjöquist in German Pat. No. 2,430,356 (Jan. 1, 1975) disclosed the methods for the qualitative or quantitative determination of various immunoglobulins, their Fc-fragments, or antigens or haptens (where the antigen or hapten is bound to the Fab-part of the immunoglobulin), using suitable polypeptides (such as "Protein A" obtained from Staphylococcus aureus). In German Pat. No. 2,557,419, Thomas Hirschfield disclosed FIA analytical reagents comprising (a) a reactive molecule (such as hapten, antigen, or antibody) with several reactive sites, one of which is capable of undergoing a specific reaction with the species to be analyzed, (b) a polyfunctional polymer lattice covalently bonded to the reactant molecule at a site sterically removed from the specific reaction site of the reactant molecule so as not to interfere with the specificity of the reagent; and (c) fluorescent dye molecules bonded to the polymer lattice in an amount insufficient to interfere with the specificity of the reagent. The polymer is preferably a polyethyleneimine having a molecular weight of 1200–60,000, and the reactant molecule is preferably an antibody (for antigen determination) of a ligand, such as dibenzylglyoxime (for the determination of polyvalent molecules). See also "Tagging allows molecule viewing,38 Industrial News Feb., 1977, page 23.

With respect to EIA, RIA, and FIA, William J. Dreyer in U.S. Pat. No. 3,853,987 (1974) disclosed the use a reagent consisting of microscopic carrier particle materials bearing (1) marker material—fluorescent compounds, radioactive compounds, or enzymes, or others—and (2) a coating of biological antibody for the substance (hapten, antigen, or antibody) whose assay is desired. The carrier is shown in the examples to be hydrolysed polyacrylamide resin, but can also be other acrylic acid derivatives, styrene polymers, agar, agarose, cellulose acetate, etc.

For a review of related subjects, see also Michel F. Aubert, "Critical Study of the Radioimmunological Assay for the Dosage of the Polypeptide Hormones in Plasma," J. Nuclear and Biological Medicine 13, 1–19 (1970); Robert Roberts, B. E. Sobel and C. W. Parker, "Radioimmunoassay for Creatine Kinase Isoenzymes," Science 194, 855–856 (Feb., 1977); Robert Roberts and A. Painter, "Radioimmunoassay for Carrier Creatine Kinase Isoenzymes, Biochimica Biophysica Acta 480, 521–526 (1977). Michael G. Grattain, J. M. Puttman, and T. G. Pretlow in "The Use of Glutaraldehyde-Conjugated Horseradish Peroxidase-Bovine Serum Albumin in the Visualization of Concanavalin A Binding to Tissue Sections of Human Colonic Tumor," Laboratory Investigation 35/6, 537–541 (1976) reported the method for the preparation of glutaraldehyde cross-linked horseradish peroxidase conjugates where bovine serum albumin (BSA) was used as the carrier, stating that soluble polymers of horseradish peroxidase linked to BSA will produce staining of greater intensity (without loss of specificity) than horseradish peroxidase monomers in the demonstration of the binding of concanavalin A to tissue sections.

Even after the teachings of U.S. Pat. No. 3,853,987, Ger. Pat. Nos. 2,430,356 and 2,557,419, as well as the literature above, what was needed in order to apply EIA and other non-isotopic technology to diseases tested formerly by RIA methods was a flexible, easily made, stable, and relatively inexpensive vehicle able to support several enzyme markers per antigen, anti-body, hapten, or other molecule of interest in order to improve the sensitivtiy of the immunoassays employed. Through the use of the novel diagnostic spine tool disclosed, not only are EIA and other non-isotropic immunoassays able to be applied with great sensitivity for quantitative and qualitative analysis of diseases such as hepatitis, rubella, and gonorrhea, but surprisingly the same spine tool of my invention can also be employed with other markers such as radioisotopes, fluorescent groups, lysis-initiating compounds etc. Likewise, the novel diagnostic tools of my invention can also be utilized to make even RIA more sensitive than available with the prior art.

SUMMARY OF THE INVENTION

Diagnostic labeled spine tools of the formula

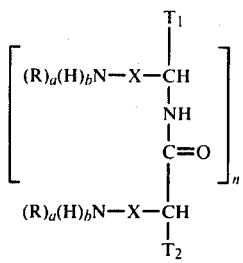

are disclosed wherein

R is an organic group labeled with a radioisotope, fluorescent group, lysis-initiating compound, enzyme or other suitable marker;

$T_1$ and $T_2$ are any of —$CH_3$,

—$CH_2OH$, —$CH_2SH$, and —$NH_2$;

X is a divalent unit selected from the group consisting of $(CH_2)_m$ where m is an integer from 0 to about 10, phenylene, hydroxyl-substituted phenylene, halogen-substituted phenylene, alkyl substituted phenylene, and aminated phenylene groups;

a is 0, 1 or 2;

b is 2-a, with the proviso that there be at least two R groups in the product, and n is a number from 1 to about 100,000.

Preferably R is an enzyme. In accordance with the present invention, the labeled spine tools are made by combining (a) any suitable water-soluble multifunctional chemical which will permit attachment of several enzyme molecules while retaining their catalytic activity and permit the covalent attachment of the compound to be labeled with (b) the predetermined marker or label, (c) under conditions which depend only on the method selected for coupling the compound to be labeled and/or the labeling moieties to the spine, an "intermediate" which may be inserted and remain between the water-soluble multifunctional chemical and the marker, or may fall out as a by product. The novel tool may then be coupled to the compound of interest by those methods to be enumerated or well known to those skilled in the art. If an enzyme marker is employed, most preferably the weight ratio of the spine tool (minus the enzyme) to the enzyme is at least about 0.3, and most preferably from about 0.3 to about 1.0. Preferably molecules of interest to be labeled are the antigens or haptens (or specific antibodies to) thyroxine ($T_4$), rubella, and gonorrhoeae, and a preferable non-isotopic label is the enzyme horseradish peroxidase.

As noted in the "Prior Art" portion of this invention, the practice heretofore has been to couple chemically one marker, for instance an enzyme to another moiety, such as a hapten, antigen, or antibody in order to allow a determination or detection of the desired antigen or antibody in the specimen to be tested. In the prior art methods, only one marker had been attached to a molecule of interest which made the determination of the marked compound comparatively difficult, the resulting compound having limited specific activity.

It is an object of the present invention to provide a labeled compound having a higher unit specific activity in given immunoassay methods than the labeled units of the prior art.

It is an object of the present invention to provide a labeled compound that contains a plurality of marker moieties available to give the user more flexibility in the use of the labeled compound.

It is yet another object of the present invention to provide a diagnostic labeled spine compound that can be used with equal facility for antibodies, antigens, and haptens.

The new materials of the present invention have at least three components being the reaction products of (a) a spine material defined with more particularity infra, (b) an enzyme or other marker moiety several of which are to be coupled per-spine molecule, and (c) depending on the coupling chemistries selected, an intermediate linking compound.

This present invention also encompasses the product of the compound or substance to be marked or labeled and the two- or three-component reaction material referred to above.

The benefits of the present invention transcend mere mechanical amplification, for the large quantities of marker which may be borne by the carrier material permit increased sensitivity for completely automated photoelectric measurement equipment for quantitative and qualitative monitoring.

DESCRIPTION OF THE PREFERRED EMBODIMENTS

A new diagnostic tool consisting of a labeled-spine material has been found for use in immunochemical methods for the detection and determination of a component of the reaction between a specific binding protein or antibody and the corresponding bindable substance, antigen, hapten, antibody, etc., applying the known binding affinity of such components for one another, characterized in that use is made of a given amount of a coupling product of the combinable substance with a novel diagnostic marked spine tool to be enumerated, and of reacting substance(s) against the specific binding protein, which may or may not be in an insolubilized form, and that after the reaction the activity of the label in the tool (the end point signal) is determined after a phase separation if necessary in the liquid or solid phase of the reaction mixture, which activity is a measure of the amount of the component to be determined. The new tool is a labeled-spine material of the formula:

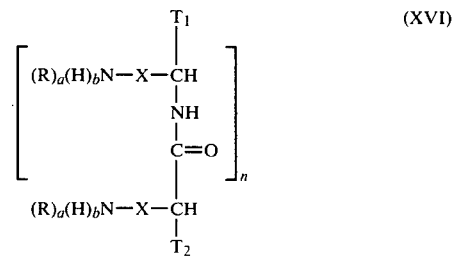

Where R is an organic group labeled with a radioisotope, fluorescent group, lysis-initiating compound, or other suitable marker material lacking a linking moiety or a combination of enzyme and linking moiety, $T_1$ and $T_2$ are any of —$CH_3$,

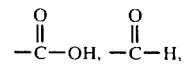

—$CH_2OH$, —$CH_2SH$, and —$NH_2$:

X is any of a divalent unit selected from the group consisting of the formula $(CH_2)_m$, where m is an integer from 0 to about 10, phenylene, hydroxyl-substituted phenylene, halogen-substituted phenylene, alkyl-substituted phenylene and animated phenylene groups;

a is 0, 1 or 2;

b is 2-a, with the proviso that there be at least two R groups in the product; and n is a number from 1 to about 100,000.

The new tool provides higher "specific activity" for labeled substances thus facilitating determination of the desired compound. By "specific activity," I mean the detectable activity per unit of volume, per unit of weight, or per unit of chemical equivalence for a given chemical. For example, if a 10 mg sample of $Ba^{14}CO_3$ assay has 100 counts per minute (cpm) using RIA, the specific activity may be reported as 10 cpm/mg $BaCO_3$, or 44.7 cpm/mg $CO_2$, or 164.1 cpm/mg C or (d) 1970 cpm/$\mu$mol. The choice of chemical equivalence is therefore left up to the user. Linking moieties may be any bifunctional compound capable of reacting specifically with the spine polymer and the marker. For a review of such compounds and their uses see for example, J. H. Kennedy, L. J. Kricka, and P. Wilding, "Protein-protein Coupling Reactions and the Applications of Protein Conjugates", Clinica Chimica Acta 70, 1-31 (1976).

1. Constituents

The invention pertains to the marking or labeling of compounds to be used in immunoassay with enzymes and other labeling moieties. Greatly augmented specific activities of the detectable property result. Specifically, my invention teaches ways of chemically coupling more than one enzyme or other labeling moiety to another molecule so that the marked or labeled molecule may be used in immunoassay with a greatly elevated specific activity. The novel compounds consist of three parts: a linking spine which is a water-soluble multifunctional molecule of appropriate chemical character and molecular weight (see infra), the enzyme or other marker moiety, more than one of which is to be coupled to the spine, and depending on the coupling chemistry selected, a linking intermediate.

The substance to be labeled is coupled to the novel tool in such a way that on the average, only one such molecule is attached per spine molecule. The product, after purification, is coupled to a large molar excess of pure marker moiety such that on the average, more than one marker moiety is coupled to each unit of linking-spine. The product is characterized, purified, and used. The final form of the high specific activity label then is, in terms of the three essential characteristics (molecule of interest)$_1$-(link-spine)$_1$-(link-marker)$_p$ where p>1; generally p is more than about 2 but less than about 5, although p may be as high as about 10. The presence of a "link" will be solely dependent upon the chemistries selected for coupling the components together.

A block functional diagram of the above may be written as follows:

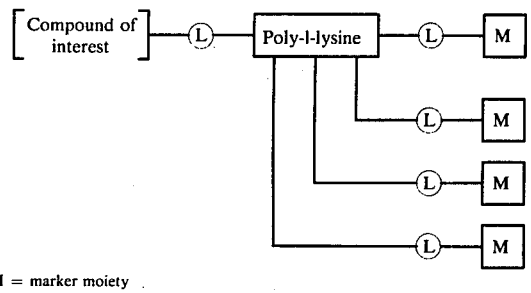

Block Functional Diagram

M = marker moiety
L = optional linking moiety

As a general criterion, and as described in more detail below, any soluble multifunctional chemical which will permit attachment of several enzyme molecules while retaining their catalytic activity and permit the covalent attachment of a compound to be labeled will serve as a spine. Any enzyme suitable for use in enzyme immunoassay may be used. Alternatively, markers other than enzymes such as fluorescent compounds, spin labeled compounds, radiolabeled compounds, etc. may be attached.

If RIA and therefore a radioisotope marker is desired to achieve high specific activity, radioisotopes are selected which have relatively short half lives. For example, $I^{125}$ ($T_{\frac{1}{2}}$=60 days) is preferred to $H^3$ ($T_{\frac{1}{2}}$=12.3 years) and $C^{14}$ ($T_{\frac{1}{2}}$=5730 years). Another preference, of course, is given to radioisotopes which are available in high isotopic purity, and which may be incorporated into a molecule at the rate of more than one atom of marker per molecule of marked substance. Suitable isotopes commonly employed are $I^{125}$ and $I^{131}$ (both incorporated into non-radioactive intermediates commonly known to those skilled in the art such as tyrosine, tyramine, histamine, histadine, and N-succinimidyl-3-(4-hydroxyphenyl) propionate and its iodinated forms), $C^{14}$ and $H^3$ (commonly known as tritium). A preferable isotope is $I^{125}$: it has a half life of about 60 days, readily reacts with most antigens, has a higher specific activity than $H^3$, $C^{14}$, or $I^{131}$, has a lower gamma energy than does $I^{131}$, and has an absence of $\beta$-radiation with absence diminishes the potential for auto distruction of the labeled antigen.

On the other hand, many of the problems commonly associated with the procurement and handling of radioisotopes may be avoided if an enzyme marker is chosen. RIA has several disadvantages, including the requirement of special equipment, trained staff, the need for extra safety measures to protect against harmful radiation, and the short half-life span of the radioactive labeling element.

The possibility of replacing the radioactive label with an enzyme label was proposed in 1968 in an article by L. E. M. Miles and C. N. Hales, entitled "Labelled Antibodies and Immunological Assay Systems," Lancet, London 1968 II, page 492; Nature, Vol. 219, pages 186-189 (July 13, 1968), put no procedural details were provided, the article failing to offer more than the general idea, leaving it to future workers to determine the basic steps and to perform the extensive experimentation needed to establish a practical operative enzymic immunoassay method. The pioneering work on enzyme-immunoassay (EIA) methodology was performed by Schuurs and coworkers, and is disclosed in a series of their U.S. Pat. Nos. 3,654,090, 3,791,932, 3,850,752, 3,839,153, and 3,879,262, 4,016,043, and Re 29,169. Now, however, enzyme-marked compounds (enzyme assay means) for use in enzyme-immunoassays should possess for successful use all of the properties with enzyme marking that were formerly held required by radioactively-labeled substances for radioimmunoassay: high specific activity (enzymatic or radioactive), chemical stability, immunologic similarity to the substance to be measured, and chemical purity. The invention described here demonstrates a method of increasing the enzymatic specific activity of a labeled substance dramatically. Of course, the same techniques can also be used to increase the specific activity of compounds labeled with radioisotopes and other marker moieties.

The choice of the enzyme which is taken up in the coupling product, is determined by a number of properties of that enzyme. It is, of course, essential that the catalytic property of the enzyme should be resistant to the coupling with another molecule. Also of great importance is the specific activity of the enzyme. As less enzyme conjugate is needed to be added to reach a measurable enzyme effect, the sensitivity of an immunoassay system can be increased. With a specified enzyme whose rate of conversion is fixed and whose purity is high, the specific activity of a labeled compound is proportional to the degree of incorporation of enzyme molecules per molecule of marked substance, and a higher specific enzymatic activity results. Additional desirable factors are a high rate of conversion of substrate, and high chemical purity. Further those enzymes are to be preferred, of which the determination of the activity can be made in a simple manner. In the first place those enzymes are considered that can be determined colorimetrically, or spectrophotometrically. These kinds of determinations are suitable for automation, which is an additional advantage.

Colorimetrically those enzymes can be determined that catalyze a reaction in which a colored substance appears or disappears.

Also, the enzyme should be stable when stored for a period of at least three months, and preferably at least six months at temperatures which are convenient for storage in the laboratory, normally −20° C. or above.

A product should be either formed or destroyed as a result of the enzyme reaction which absorbs light in the ultra-violet region or the visible region, that is in the range of about 250-750 nm, preferably 300-600 nm.

The enzyme should have a satisfactory turnover rate at or near the pH optimum for immunoassay conditions, this is normally at about pH 6-10, usually 6.0 to 8.0. Preferably, the enzyme will have the pH optimum for the turnover rate at or near the pH optimum for binding of the antibody to the ligand.

The enzyme which is employed or other enzymes, with like activity, will not be present in the fluid to be measured, or can be easily removed or deactivated prior to the addition of the assay reagents. Also, one must insure that naturally occurring inhibitors for the enzyme present in fluids to be assayed are not present in concentrations at which they will interfere.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight limitations refer to the enzyme and not to the subunits.

A summary of properties of enzymes useful for enzyme labels is given below:
1. Available and inexpensive in high purity.
2. High enzymatic specific activity.
3. Soluble under labeling and assay conditions.
4. Chemically and functionally stable under labeling and assay conditions.
5. Enzymatic activity detected simply, sensitively, inexpensively, rapidly and with standard laboratory equipment.
6. Missing or in negligible concentration in analysis.
7. Interfering factors missing in analyte.

Enzymes currently used as labeling moieties in enzyme immunoassay (from G. B. Wisdom, Clinical Chemistry 22, No. 6, 1243-1255 (1976)) are shown in Table II.

Table II

| Enzyme | Source | Enzyme Commission No. |
|---|---|---|
| Malate dehydrogenated | Pig heart mitochondria | 1.1.1.37 |
| Glucose-6-phosphate dehydrogenated | *Leuconostoc mesenteroides* | 1.1.1.49 |
| Glucose oxidase | Fungal | 1.1.3.4 |
| Peroxidase | Horse-radish | 1.11.1.7 |
| Acetylcholinesterase | | 3.1.1.7 |
| Alkaline phosphatase | Calf intestinal mucosa and *E. coli* | 3.1.3.1 |
| Glucoamylase | *Rhizopus nivens* | 3.2.1.3 |
| Lysozyme$^a$ | Egg white | 3.2.1.17 |
| β-Gatactosidase | *E. coli* | 3.2.1.23 |

Preferable enzymes generally include catalase, peroxidases, β-glucosoindase, β-D-glucosidase, β-D-galactosidase, urease, glucose oxidase, galactose oxidase, and alkaline phosphatase; in general the glucuronidases, galactosidases, ureases and the oxidoreductases. An extremely preferable enzyme is horseradish peroxidase (HRPO) which can be obtained relatively inexpensively for pure material, has a high converstion of substrate, and has a substantially flat fixed rate of conversion.

Use of an enzyme immunoassay system offers attractive advantages: elimination of radioactive substances and their associated hazards and license requirements, common, inexpensive laboratory equipment used, amplification of results through repeated use of enzyme catalysts (a radioisotopic atom decays only once) and ready availability commercially of the enzymes. Unlike radioactively labeled compounds where high specific radioactivities lead to increased auto-radiolytic destruction, these high specific enzymatic activity enzyme systems are stable chemically, there being no radioactive emissions present to cause destruction. Hence, preferable markers for my invention are suitable enzymes, with HRPO being most preferable.

As known to those skilled in the art, in some instances a "cofactor" or coenzyme, which is a small nonprotein prosthetic group (i.e., compound), is required before an enzyme can exert its catalytic effect on a substrate. An example of such an enzyme is malate dehydrogenase.

Fluorescent markers yield overall reaction-detection sensitivities which, though a great deal better than those obtainable with radioactive and other sorts of tags are workable in my invention but still leave much to be desired.

Nevertheless, such markers have been used extensively for localization of specific constituents at the outer surfaces of cells, or within cells—that is, in cytology. Fluorescent marker work with immune reactants, generally known as "immuno-fluorescence", has heretofore been put to use primarily in cytology. Since cells are in a sense particles, the distinction between immuno-fluorescence and parts of the present invention is essential. In immuno-fluorescence the biological cells ("particles") are themselves the objects of a screening survey; while in the present invention the particles (or other carrier forms) are part of a chemical tool used for assays and separations of other substances, as explained later.

Fluorescent markers have also been used in other immunological work—but heretofore generally in such other instances the tracer molecules have simply been added or attached to immune reagent molecules on a roughly one-to-one basis.

Examples of fluorescent markers may be shown in the following table:

TABLE II—Suitable Fluorescent Groups

Acridine Orange
5-Amino-2,3-dihydro-1,4-phthalazinedione
7-Amino-1,3-naphthalenedisulfonic Acid
4-Amino-1-naphthalenesulfonic Acid
p-Anisaldehyde
Chromotropic Acid
Coumarin
2',7'-Dichlorofluorescein
6,7-Dihydroxy-4-methylcoumarin
Eosin
Erythrosin
Fluorescamine
Fluorescein
1-Hydroxy-2-naphthoic Acid
3-Hydroxy-2-naphthoic Acid
trans-o-Hydroxycinnamic Acid
4-Methylumbelliferone
Morin
1-Naphthol
2-Naphthol
1-Naphthol-3,6-disulfonic Acid
2-Naphthol-6,8-disulfonic Acid
1-Naphthol-2-sulfonic Acid
1-Naphthol-4-sulfonic Acid
2-Naphthol-6-sulfonic Acid
1-Naphthylamine
o-Phenylenediamine
p-Phenylenediamine
Phloxine B
Resourfin
Rhodamine
Salicylic Acid
2',4',5',7'-Tetrabromofluorescein Preferable fluorescent groups include fluorescein, rhodamine, fluorescamine, rhodamine, and 8-anilino-1-naphthalene sulfonic acid. A most preferable fluorescent group is fluorescein.

As will be recognized by those skilled in the art, other non-isotopic markers or labels are available as markers in lieu of enzymes or fluorescent groups: erythrocytes, stable free radicals, bacteriophages, etc. In immunoassays using any of these labels the marked component of an antibody/antigen reaction binds to its complimentary binding site. The amount bound depends on the concentrations of other components of the system. If the unlabeled component similar to the component to be analyzed is varied in a regular way, changes in the distribution of the marked component on the binding protein occurs. The particular properties of the marker are used to determine this distribution, and thus a calibration curve can be constructed relating distribution of the label to the concentration of the component varied.

The term "antibody" or "antibodies" is employed herein to mean a group of serum proteins, also referred to as gamma globulins or immunoglobulins, that will specifically react with an antigen or hapten. Most of these antibodies belong to the IgG class, while the other classes are termed IgA, IgM, IgD, and IgE. It is also used herein to include certain naturally occurring binding proteins which recognize certain humoral constituents, for example such proteins for testosterone, cortisol and thyroxine.

The term "antigen" is employed herein to mean a substance that will react with an antibody. Antigens are often characterized as capable of inducing the formation of an antibody and of reacting with that antibody. However, as will be discussed herein below, in the case of "haptens" is it necessary to be coupled to a carrier, such as, for example, inert adsorbing particles, synthetic peptides, or natural protein molecules, in order to induce antibody formation. Materials commonly employed as carriers include for example, the albumins (human, bovine, or rabbit), synthetic polypeptides (for example, polylysine), inert adsorbing particles (for example, charcoal particles) and polymers (example, dextrans). However, haptens will in the absence of a carrier still react with antibodies and can be employed in the antigen-antibody reaction assays of the present invention either with or without carriers.

The term "pure protein" or simply "protein" as employed herein is intended to include proteins and polypeptides that are free of contamination, and it is good practice to use such pure material to avoid unnecessary interfering factors.

The following Table III lists a partial representation of diseases, causative organisms, antigens, and antibodies within the scope of the invention:

TABLE III

REPRESENSTATIVE ANTIGENS AND ANTIBODIES

Disease States and Antigen Derived From the Causative Organism or Other Specific Antigens Used in the Diagnosis of Certain Disease States I. Infectious Diseases.
A. Parasites.

| Disease | Organism | Antigen |
|---|---|---|
| Amoebiasis | Entamobia histolytica | Organism sonicate of strain HK-9 |
| Toxoplasmosis | Toxoplasma gondii | Whole organism or there sonicate derived from tissue culture or mouse peritoneal fluid |
| Changes | Typanosoma cruzi | Organism sonicate derived from tissue |

TABLE III-continued
REPRESENSTATIVE ANTIGENS AND ANTIBODIES
Disease States and Antigen Derived From the
Causative Organism or Other Specific Antigens
Used in the Diagnosis of Certain Disease States

|  |  |  | |
|---|---|---|---|
| | Schistosomiasis | Schistosoma haematobium | culture |
| | | Schistosome japonicum | |
| | | Schistosoma mansoni | Culture filtrates |
| B. | Bacteria | | |
| | Infectious meningitis | Neisseria meningitidis | Capsular polysaccharide |
| | Gonorrhea | Neisseria gonorrheae | Pili isolated from the bacterial cells |
| | Typhoid fever | Salmonella typhi | Bacterial cells or their extracts |
| | Phenumonia Diplococcus pheumoniae | Capsular polysaccharide | |
| C. | Fungi | | |
| | Histoplasmosis | Histoplasma capsulatum | Culture filtrate |
| | Blastomycosis | Blastomyces dermatitidis | Culture filtrate |
| | Coccicioidomycosis | Coccidivides immitis | Culture filtrate |
| D. | Viruses | | |
| | Rubella | Rubella virus | Virus particles |
| | Measles | Measles virus | Virus particles |
| | Rabies | Rabies virus | Virus particles |
| 2. | Allergies | | |
| | | Ragweed pollen | Pollen extract |
| | | Tomatoes | Tomato extract |
| | | Bermuda grass seed | Seed extract |
| | | Cat dander | Fur extract |
| | | House dirt | Dust extract |
| 3. | Disease States | | |
| | Lupus erythermatosis | DNA molecules | |
| | | RNA molecules | |
| | Rheumatoid arthritis | Human IgG | |
| | Colon | cancer | CFA antigen |
| | Hepatoma | Alpha-1-feto protein | |

The novel tools of my invention can also be employed for the determination of haptens, which may be regarded as a special group of low molecular compounds, and their anti-substances. These substances mostly occur in low concentrations. According to the original definition of K. Landsteiner, haptens are protein-free substances whose chemical configuration is such that they can react with specific antibodies, but not such that they are capable of causing the formation of antibodies. In order to be able yet to make antibodies against haptens, the haptens must be coupled to polypeptides, inert adsorbing particles, or natural protein molecules before being injected into a test animal. In the determination of a low molecular weight compound by classical immunoassay, the substance to be determined and its coupling product with an enzyme enter into competition for a given quantity of the insoluble specific binding protein. The more unlabeled compound the sample contains, the less opportunity the soluble enzyme conjugate of that compound has to combine with the specific binding protein and the more of the conjugate will remain unbound in the liquid phase. Following a separation of bound and free phases (frequently but now always necessary), the enzyme activity can be measured in a single manner.

As examples of haptens are mentioned: steroids, such as estrone, estradiol, estriol, cortisol, cortisone, testosterone, pregnanediol, and progesterone; vitamins, such as vitamin $B_{12}$ and folic acid; 1-thyroxine, triiodo-1-thyronine, histamine, serotonin, digoxin, prostaglandin, adrenalin, nor-adrenalin, morphine, vegetable hormones, such as auxin, kinetin and gibberellic acid, and antibiotics, such as penicillin.

Hence the compound or substance to be labeled is a conventional diagnostic material such as hapten, a drug, a hormone, a protein, nucleic acid or other biologically or immunologically useful or interesting molecule, or viruses or bacteria.

As indicated below, a number of methods are available for immunoassays using various different labeled systems, some requiring separation of free and bound label through the use of one component of the antigen-antibody reaction being in an "insolubilized" form (e.g. U.S. Pat. Nos. 3,654,090; 3,791,932; 3,839,153; 3,850,752; 3,879,262; 4,016,043; and U.S. Re. Pat. No. 29,169 all incorporated herein by reference for EIA methods) and other methods not requiring separation of free and bound label because the assay depends on inhibition or activation of the enzyme label by antibody binding (e.g., the so-called EMIT ® system of Syva Corporation of Palo Alto, California for EIA and FRAT, or "free radical assay technique" for SIA). With respect to methods employing "insolubilized" components, some elaboration is necessary.

The term "novel marker-spine material", "diagnostic marker-spine material", "diagnostic marker-spine tool", "marker-spine material" and "spine material product", or variations thereof, are used interchangeably to denote the same novel compounds or reagents of our invention.

Basically, any water-soluble multifunctional chemical which will permit attachment of several enzyme or other marker moieties while retaining their catalytic activity (e.g., the water-soluble proteins, homopolyamino acids, multichain amino acids, sequential polypeptides, random polypeptides, dextrans, water-soluble celluloses, polysaccharides, etc., as will be delineated herein after) and permit the covalent attachment of a compound to be labeled will serve as the basis for the novel diagnostic marker spine tools of my invention. Preferably, these water soluble multifunctional chemicals are of the following formula:

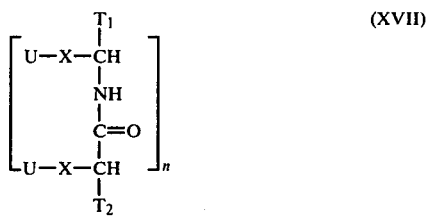

where $T_1$ and $T_2$ are polymeric terminators, preferably selected from the group consisting of —$CH_3$,

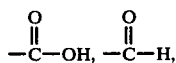

—$CH_2OH$, —$CH_2SH$, and —$NH_2$; U is a reactive organic moiety and monomeric-end terminator selected from the group consisting of

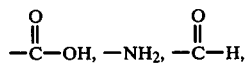

—$CH_2OH$, and —$CH_2SH$; X is a divalent unit selected from the group consisting of $(CH_2)_m$, where m is an integer from 0 to about 10, phenylene, hydroxyl-substituted phenylene, halogen-substituted phenylene, alkyl-substituted phenylene and aminated phenylene groups; and n is a number from one to about 100,000. Preferably, one of $T_1$ and $T_2$ is

and the other of $T_1$ and $T_2$ is $NH_2$; likewise and preferably, U is $NH_2$. In general, any preferable polymer can be made readily from derivatives of monomeric aminoacid of the formula:

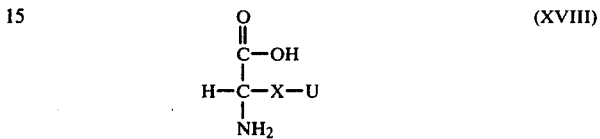

having the same nomenclature as above. Acid anhydrides (so called Leuck's anhydrides), of these monomers will combine easily in a condensation reaction according to methods known to those in the art. See paragraph 31.35, L. F. Fieser and M. Fieser, *Advanced Organic Chemistry*, Reinholt Publishing Corporation, New York (1961), pages 1060–1061. Illustrating the condensation reaction with glycine (which is not a suitable monomer (III) but will serve as an illustration of the condensation of amino acid monomers to polyamino acids.

Reaction 1

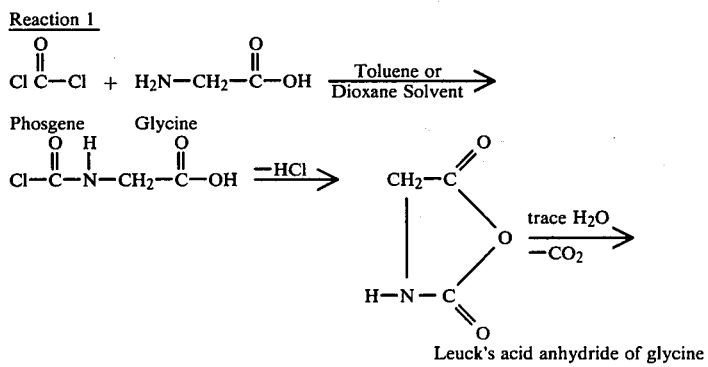

Leuck's acid anhydride of glycine

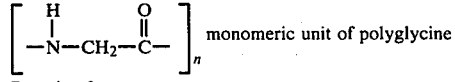

Reaction 2

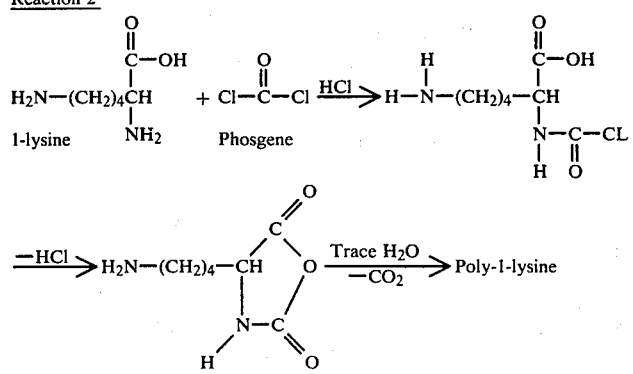

It may be noted that U may not only be one of the preferable groups mentioned above (e.g.,

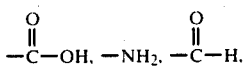

—CH₂OH and —CH₂SH), but may also be —OH, —SH,

(secondary amines),

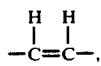

and if protein molecules are utilized for the polymer, the following:

TABLE IV
U GROUPS IN AMINO ACIDS

| Reactive Group | Residue |
|---|---|
| Amide —C(=O)—N(H)— | Asn, Gln |
| Amino, imino —N(H)— | Arg, His, Lys, Try |
| Phenyl —C₆H₄— | Phe, Try, Tyr |
| Carboxyl —C(=O)—OH | Asp, Gln |
| Hydroxyl —OH | Ser, Thr, Tyr |
| Phenolic —C₆H₄—OH | Tyr |
| Thiol —SH | CysH |

For well-known methods to produce the water-soluble multifunctional chemicals necessary to our invention from the corresponding monomers, see paragraph 31.35, L. F. Fieser and M. Fieser, *Advanced Organic Chemistry*, Reinholt Publishing Corporation, New York., (1961), pages 1060–1061. Examples of suitable water soluble multifunctional chemicals are shown in the following table:

TABLE V
SUITABLE POLYMERS

1. Homopolyamino Acids

Poly Arginine HCl
    Poly-L-Arginine . HCl
    Poly-L-Arginine . Sulfate
    Poly Asparagine
    Poly Aspartic Acid
    Poly-L-Aspartic Acid
    Poly-β-Benzyl Aspartate
    Poly-β-Benzyl-L-Aspartate
    Poly Benzyl Cysteine
    Poly-S-CBZ-Cysteine
    Poly-S-CBZ-L-Cysteine
    Poly-γ-Benzyl-Glutamate
    Poly-γ-Benzyl-L-Glutamate
    Poly Methyl Glutamate
    Poly-γ-Methyl-L-Glutamate
    Poly Glutamic Acid
    Poly-D-Glutamic Acid
    Poly-L-Glutamic Acid
    Poly Ornithine HBr
    Poly-α-Ornithine HBr
    Poly-α-Ornithine Hydrobromide
    Poly Phenylalanine
    Poly-L-Phenylalanine
    Poly-L-Proline
    Poly Sarcosine
    Poly-o-Acetyl Serine
    Poly Homoserine
    Poly-o-CBZ-Serine Poly-γ-Hydroxypropyl Glutamide
    Poly N⁵ (3-hydroxy propyl) L-Glutamine
    Poly-L-Histidine
    Poly-im-Benzyl Histidine
    Poly Histidine
    Poly Acetyl Hydroxyproline
    Poly-D-Lysine Hydrobromide
    Poly-DL-Lysine Hydrobromide
    Poly-L-Lysine Hydrobromide
    Polylysine (PLL or Poly Lysine)
    Poly-L-Lysine HCl
    Poly-ε-CBZ-Lysine
    Poly-ε-CBZ-L-Lysine
    Poly Methionine
    Poly-L-Methionine
    Poly-δ-CBZ-Ornithine
    Poly Ornithine
    Poly-L-Serine
    Poly Lysine, Succinylated
    Poly Thyleneinine
    Poly Tryptophan
    Poly-DL-Tryptophan
    Poly-L-Tryptophan
    Poly-o-Acetyl Tyrosine
    Poly-CBZ-Tyrosine
    Poly-L-Tyrosine
    Poly-o-CBZ-L-Tyrosine 2. Multichain polyamino Acids

Multichain Poly-DL-Alanyl-Poly-L-Lysine
    Multichain Poly (L-Tyrosine:L-Glutamic Acid)-Poly-DL-Alanine-Poly-L-Lysine 4. Sequential Polypeptide

Poly(L-Prolyl-Glycyl-L-Prolyl)

5. Random Polypeptides

D-Glutamic Acid Copolymer
    L-Lysine:L-Tyrosine Copolymers, HBr Salts

L-Glutamic Acid Copolymers
    L-Lysine Copolymers, HBr Salts

6. Water soluble Polysaccharides.

The following is a partial list of water-soluble polysaccharides taken from Scientific Tables, Seventh Edition Documenta Geigy, CIBA-GEIGY Ltd., Basle, Switzerland (1970):

| Name | Mol.Wt. | Structure | Specific Rotation |
|---|---|---|---|
| Atnylopectin (α-amylose, B-fraction of starch) | Up to 52 × 10⁴ for potato amylopectin | Highly-branched molecule composed of several hundred unit chains, each of which comprises 20–26 α-1:4-linked glucose residues; the unit-chains are inter-linked by glycosidic bonds from the reducing group to C-6 of a glucose residue in an adjacent chain: | $[\alpha]_D^H + 150°$ |

TABLE V-continued
SUITABLE POLYMERS

| | | | |
|---|---|---|---|
| Amylose (β-amylose A-fraction of starch) | (323) up to 1 × 10⁴ | Essentially a linear chain of α-1:4 linked glucose residues: | $[α]_D^H + 220°$ |
| Bacterial capsule polysaccharides | — | Polymers with a composition depending on the type of organism. Thus, the polysaccharide of pneumococcus type II is composed of glucose, glucuronic acid and rhamnose that of pneumococcus type III of glucose and glucuronic acid, that of pneumococcus type XIV of glucose galactose and N-acetylglucosamine, that of streptococci groups A and C of glucuronic acid and N-acetylglucosamine, that of Haemophilus influenzae of ribose phosphate. Probable structure of the polysaccharide of pneumococcus type III: | — |
| Bacterial cell-wall polysaccharides (murcins) | — | Very large macromolecules of complex structure. The amino sugars N-acetylglucosamine and N-acetyl muramic acid form strands of linear unbranched muropolysaccharides making up the backbone of the murcin. These strands are attached by amide bonds to the carboxylic groups of the muramic acids and carry short oligopeptide side chains. Additional peptide bonds occur between different side chains of neighbouring muropolysaccharide strands, so that a close two- or three-dimensional mesh is formed. | — |
| Chitin | (203.19) ca.4 × 10⁶ | Linear chain of β-1:4 linked N-acetyl-D glucosamine residues: | $[α]_D^H - 14.7°$ (in HCl) |
| Chondroitin sulphate A (chondroitin | Polydisperse | Polymer composed of D-glucuronic acid, N-acetyl-D-galactosamine and sulphate residues. Probable structure: | $[α]_D$ -28° to -32° |

TABLE V-continued
SUITABLE POLYMERS 4-sulphate)

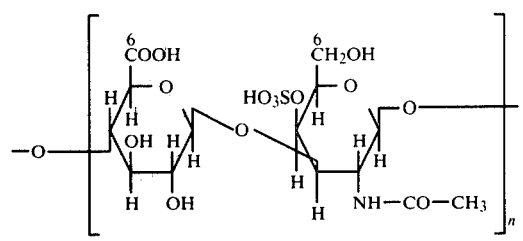

| Chondroitin sulphate B (β-heparin dermatan sulphate) | Polydisperse | Polymer composed of L-iduronic acid, N-acetyl-D-galactosamine and sulphate residues. Probable structure: | $[\alpha]_D - 60°$ to$-32°$ |

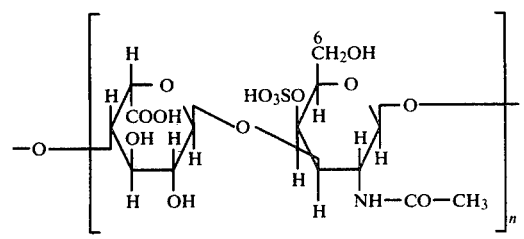

| Chondroitin sulphate C (chondroitin 6-sulphate) | Polydisperse | Polymer composed of D-glucuronic acid, N-acetyl-D-galactosamine and sulphate residues. Probable structure: | $[\alpha]_D - 16°$ to$-22°$ |

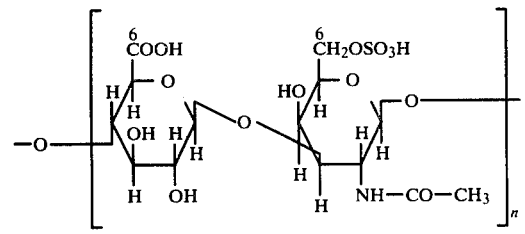

| Hyaluronic acid | ca. $1 \times 10^4$ | Polymer composed of N-acetyl-D-galactosamine and D-glucuronic acid residue. Probable structure: | — |

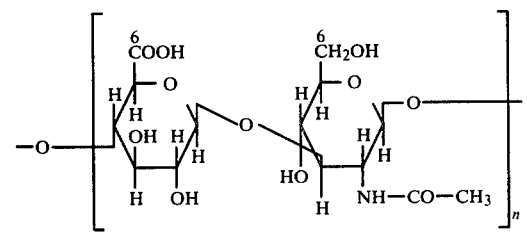

| Inulin | (162.14) ca. 5000 | Linear chain of about 30 β-1:2-linked fructo-furanose units: | $[\alpha]_D^H - 40°$ |

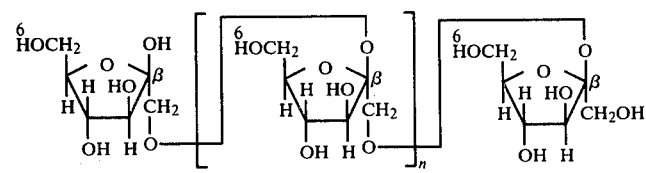

| Keratan sulphate (kerato-sulphate) | Polydisperse | Polymer composed of D-galactose N-acetyl-D-glucosamine and sulphate residues. It is probably (1→ 3)-O-β-D-galactopyranosyl-(1→ 4)-2-acetamido-2-deoxy-6-O-sulpho-β-D-gluco-pyranose | — |
| Pectic acid (pectins) | (346) up to $5 \times 10^4$ | Probably a linear chain of α-1:4-linked D-galacturonic acid residues: | $[\alpha]_D^H$ ca + 240° |

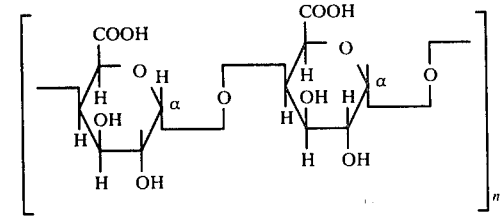

TABLE V-continued
SUITABLE POLYMERS

| | | | | |
|---|---|---|---|---|
| Teichoic acids | — | Linear polymers of either glycerol or ribitol phosphate subunits connected in 1,3- or 1,5-phosphodiester linkages respectively. The hydroxyl groups of the polyol monomers may be substituted with D-alanine in an ester bond and with different glycosidically linked mono- or oligosaccharides functioning as the determinant groups of the teichoic acid antigens | | — |
| Dextrans | (323) ca. $4 \times 10^4$ | Probably $\alpha$-1:6-linked glucose residues in branched or straight chains, for instance: | | — |
| Glycogen (liver starch) | Polydisperse; for most glycogens at least $2 \times 10^4$ | Highly-branched molecule resembling amylopectin and consisting of unit chains of $\alpha$-L:4-linked glucose residues interlinked by $\alpha$-1:6-glycosidic bonds: | | $[\alpha]_D^H$ ca. $+ 200°$ (water) |

7. Monomeric Amino-Acid Units before Polymerization:
   the following represents monomeric amino-acid units before polymerizations, and is a partial list of water-soluble amino acid units taken from Table VII, Scientific Tables, Seventh Edition Documenta Geigy, CIBA-GEIGY Ltd., Basle, Switzerland (1972):

| Name | Symbol | Formula and mol.wt. | Structure | Elementary composition (%). | | | Solubility (grammes per 100g water at 25° C.) |
|---|---|---|---|---|---|---|---|
| | | | | C | H | N | |
| Arginine ($\alpha$-amino-$\delta$-guanido-n-valeric acid) | Arg | $C_6H_{14}N_4O_3$ 174.20 | HN$\diagdown$<br>$\quad$C—NH—(CH$_2$)$_3$—<br>H$_2$N$\diagup$<br>CH(NH$_2$)—COOH | 41.37 | 8.10 | 32.16 | 15 |
| Asparagine (Aspartic acid $\beta$-mono-amide; $\alpha$-amino-$\beta$-carbamyl-propionic acid) | Asn or Asp(NH$_2$) Asp$\vert$NH$_2$ | $C_4H_8N_2O_3$ 132.12 | NH$_2$—CO—CH$_2$—CH—(NH$_2$)—COOH | 36.36 | 6.10 | 21.20 | 2.46 |
| Aspartic acid (aminosuccinic acid) | Asp | $C_4H_7NO_4$ 133.10 | HOOC—CH$_2$—CH—(NH$_2$)—COOH | 36.10 | 5.30 | 10.52 | 0.50 |
| Cysteine ($\alpha$-amino-$\beta$-thiolpropionic acid) | Cys | $C_2H_7NO_3S$ 121.16 | HS—CH$_2$—CH(NH$_2$)—COOH<br>Sulphur 26.46 | 29.74 | 5.82 | 11.56 | Very soluble |
| Cystine (di-[$\alpha$-amino-propionic]-$\beta$-disulphide) | Cys$\vert$Cys | $C_4H_{12}N_3O_4S_2$ 240.30 | S—CH$_2$—CH(NH$_2$)—COOH<br>$\vert$<br>S—CH$_2$—CH(NH$_2$)—COOH<br>Sulphur 26.69 | 29.99 | 5.03 | 11.66 | 0.011 |

TABLE V-continued
SUITABLE POLYMERS

| Name | Symbol | Formula and mol.wt. | Structure | | | | |
|---|---|---|---|---|---|---|---|
| 3,5-Di-iodo-tyrosine*** | — | $C_9H_9NO_3I_2$ 432.99 | HO—⬡(I)(I)—$CH_2$—CH— (NH$_2$)—COOH | 24.97 Iodine 58.62 | 2.10 | 3.23 | 0.062 |
| Glutamic acid (α-aminoglutaric acid) | Glu | $C_5H_9NO_4$ 147.13 | HOOC(CH$_2$)$_2$—CH(NH$_2$)—COOH | 40.82 | 6.17 | 9.52 | 0.843 |
| Glutamine (glutamic acid β-mono-amide; α-amino-γ-carbamyl butyric acid) | Gln or Glu (NH$_2$) of Glu\|NH$_2$ | $C_5H_{10}N_2O_3$ 146.15 | NH$_2$—CO(CH$_2$)$_2$—CH(NH$_2$)—COOH | 41.09 | 6.90 | 19.17 | 3.6 (at 18° C.) |
| Histidine (α-amino-β-[4-imidazole]-propionic acid) | His | $C_6H_9N_3O_2$ 155.16 | HC=C—CH$_2$— \| \| HN  N  \ //  C  H  CH(NH$_2$)—COOH | 46.45 | 5.85 | 27.08 | 4.29 |
| δ-Hydroxy-lysine (α,ε-diamino-δ-hydroxy-n-caproic acid) | Hyl | $C_6H_{14}N_2O_3$ 162.19 | NH$_2$—CH$_2$—CH—(OH)—(CH$_2$)$_2$—CH(NH$_2$)—COOH | 44.43 | 8.70 | 17.27 | — |
| Lysine (α,ε-diamino-n-caproic acid) | Lys | $C_6H_{14}N_2O_2$ 146.19 | NH$_2$—(CH$_2$)$_4$—CH(NH$_2$)—COOH | 49.30 | 9.65 | 19.16 | Very soluble |
| Phenylalanine (α-amino-β-phenyl-propionic acid) | Phe | $C_9H_{11}NO_2$ 165.19 | ⬡—CH$_2$—CH— (NH$_2$)—COOH | 65.44 | 6.71 | 8.48 | 2.965 |
| Serine (α-amino-β-hydroxy-propionic acid) | Ser | $C_3H_7NO_3$ 105.09 | HO—CH$_2$—CH—(NH$_2$)—COOH | 34.29 | 6.71 | 13.33 | 5.023 (for DL-acid) |
| Valine (α-amino-trivaleric acid) | Val | $C_5H_{11}NO_2$ 117.15 | (CH$_3$)$_2$CH—CH (NH$_2$)—COOH | 51.26 | 9.46 | 11.96 | 8.85 |
| Ornithine (2,5-diamino-n-valeric acid) | | $C_5H_{12}N_2O_2$ 132.16 | NH$_2$—(CH$_2$)$_3$—CH(NH$_2$)—COOH | 45.44 | 9.15 | 21.20 | Very soluble |

| Name | Symbol | Formula and mol.wt. | Structure | Temperature (°C.) | Concentration** | Solvent | $[\alpha]_D$ |
|---|---|---|---|---|---|---|---|
| Arginine (α-amino-δ-guanido-n-valeric acid) | Arg | $C_6H_{14}N_4O_3$ 174.20 | HN\\ C—NH—(CH$_2$)$_3$— / H$_2$N CH(NH$_2$)—COOH | 23.3 20 20 | 1.65 3.48 0.87 | 6-n HCl Water 0.5-n NaOH | + 27.58 + 12.5 + 11.8 |
| Asparagine (Aspartic acid β-mono-amide; α-amino-β-carbamyl-propionic acid) | Asn or Asp(NH$_2$) Asp \| NH$_2$ | $C_4H_8N_2O_3$ 132.12 | NH$_2$—CO—CH$_2$—CH—(NH$_2$)—COOH | 20 20 20 | 2.24 1.41 11.23 | 3.4-n HCl Water 2.5-n NaOH | + 34.26 − 5.30 − 6.35 |
| Aspartic acid (aminosuccinic acid) | Asp | $C_4H_7NO_4$ 133.10 | HOOC—CH$_2$—CH—(NH$_2$)—COOH | 24 18 18 | 2.02 1.33 1.33 | 6-n HCl Water 3-n NaOH | + 24.6 + 4.7 − 1.7 |
| Cysteine (α-amino-β-thiolpropionic acid) | Cys | $C_2H_7NO_3S$ 121.16 | HS—CH$_2$—CH(NH$_2$)—COOH | 26 | 12.1 | 1-n HCl | + 7.6 |

TABLE V-continued
SUITABLE POLYMERS

| | | | | | | | |
|---|---|---|---|---|---|---|---|
| Cystine (di-[α-amino-propionic]-β-disulphide) | Cys \| Cys | $C_4H_{12}N_3O_4S_2$ 240.30 | S—$CH_2$—$CH(NH_2)$—COOH<br>S—$CH_2$—$CH(NH_2)$—COOH | 24<br>18.5 | 1.0<br>0.4 | 1-n HCl<br>0.2-n NaOH | −214.4<br>− 70.0 |
| 3,5-Di-iodo-tyrosine*** | — | $C_9H_9NO_3I_2$ 432.99 | 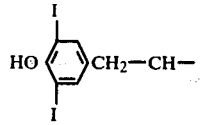<br>$(NH_2)$—COOH | 20<br>20 | 5.08<br>4.41 | 1.1-n HCl<br>3.4-n $NH_4$—OH | + 2.89<br>+ 2.27 |
| Glutamic acid (α-aminogluta-ric acid) | Glu | $C_5H_9NO_4$ 147.13 | $HOOC(CH_2)_2$—$CH(NH_2)$—COOH | 22.4<br>18<br>18 | 1.00<br>1.47<br>1.47 | 6-n HCl<br>Water<br>1-n NaOH | + 31.2<br>+ 11.5<br>+ 10.96 |
| Glutamine (glutamic acid β-mono-amide; α-amino-γ-carbamyl butyric acid) | Gln or Glu of Glu \| $NH_2$ | $C_5H_{10}N_2O_3$ 146.15 | $NH_2$—$CO(CH_2)_2$—$CH(NH_2)$—COOH | 22 | 3.6 | Water | + 5.0 |
| Histidine (α-amino-β-[4-imida-zole]-propi-onic acid) | His | $C_6H_9N_3O_2$ 155.16 | 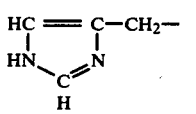<br>$CH(NH_2)$—COOH | 25<br>25<br>20 | 1.00–4.05<br>0.75–3.77<br>0.77 | 6.1-n HCl<br>Water<br>0.5-n NaOH | + 13.34<br>− 38.95<br>− 10.9 |
| δ-Hydroxy-lysine (α,ε-diamino-δ-hydroxy-n-caproic acid) | Hyl | $C_6H_{14}N_2O_3$ 162.19 | $NH_2$—$CH_2$—CH—(OH)—$(CH_2)_2$—$CH(NH_2)$—COOH | 25 | 2.0 | 6-n HCl | + 14.5 |
| Lysine (α,ε-diamino-n-caproic acid) | Lys | $C_6H_{14}N_2O_2$ 146.19 | $NH_2$—$(CH_2)_4$—$CH(NH_2)$—COOH | 23<br>20 | 2.00<br>6.50 | 6-n HCl<br>Water | + 25.9<br>+ 14.6 |
| Phenylala-nine (α-amino-β-phenyl-propionic acid) | Phe | $C_9H_{11}NO_2$ 165.19 | 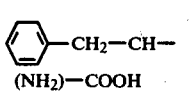<br>$(NH_2)$—COOH | 20 | 1.93 | Water | − 35.14 |
| Serine (α-amino-β-hydroxy-propionic acid) | Ser | $C_3H_7NO_3$ 105.09 | HO—$CH_2$—CH—$(NH_2)$—COOH | 25<br>20 | 9.34<br>10.41 | 1-n HCl<br>Water | + 14.95<br>− 6.83 |
| Valine (α-amino-trivaleric acid) | Val | $C_5H_{11}NO_2$ 117.15 | $(CH_3)_2CH$—CH $(NH_2)$—COOH | 20<br>20 | 3.4<br>3.58 | 6-n HCl<br>Water | + 28.8<br>+ 6.42 |
| Ornithine (2,5-diamino-n-valeric acid) | | $C_5H_{11}N_2O_2$ 132.16 | $NH_2$—$(CH_2)_3$—$CH(NH_2)$—COOH | 20 | 0.84 | 0.45-n HCl | + 14.1 |

It is necessary often to "direct" the chemistry, i.e., to control the reaction sequence by two or more step processes as outlined below, the steps being at different temperatures, pressures, or concentrations of reactants to permit the incorporation of appropriate molar ratios of the ingredients making up the spine label.

For example, it is sometimes desirable to use "intermediates" to direct the chemistry in an appropriate way, e.g., to control in a better fashion the molar relationship between the spine polymer material and the molecule of interest so as to avoid multiple incorporation of the antigen. Second, in some instances (such as thyroxine or $T_4$), the molecule of interest will not in itself readily combine with a predetermined polymer (such as polylysine or PLL). Hence, as those well skilled in the art will appreciate, it is desirable to combine the molecule of interest (for example, $T_4$) with an intermediate and then react this linking or activated moiety with the predetermined water-soluble multifunctional compound.

In some chemical coupling schemes, portions of the coupling molecules (or intermediates) will remain inserted between the molecule of interest and spine; in other cases this will not occur (see Case 3 below). Listed below are two examples of the former occurrence and two examples of the latter, using $T_4$ as the molecule of interest, polylysine (PLL) as the polymer, and various compounds as causal agents to effect chemical coupling of molecule of interest to spine (tolylene-2,4-diisocyanate, glutaraldehyde, and carbodiimide). The novel tools manufactured are especially suitable for use in an EIA application with horseradish peroxidase as the marking moiety:

CASE 1: Intermediate Remains with PLL; Tolylene-2,4-diisocyanate (TDIC) coupling of $T_4$ to PLL:

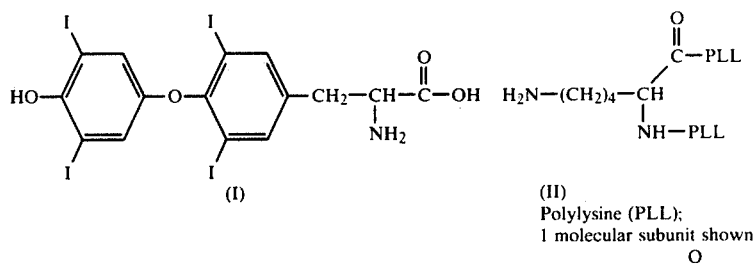

(I)

(II) Polylysine (PLL); 1 molecular subunit shown

Thyroxine (T₄); sometimes referred to below as NH₂—(T₄) and otherwise as (T₄)—C(=O)—OH depending on which portion of the T₄ molecule participates in the coupling reaction.

(3)

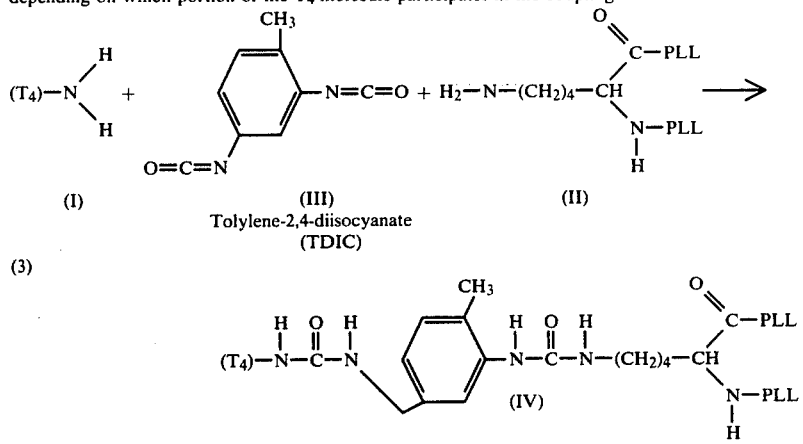

(I)    (III) Tolylene-2,4-diisocyanate (TDIC)    (II)

(IV)

Here the TDIC molecule is inserted permanently into the chemical structure as an intermediate. This reaction may be conducted from about −20° C. to about 40° C. and preferably at about −10° C.; a suitable solvent is dimethylformamide.

CASE 2: Schiff-base condensation reaction with intermediate remaining: glutaraldehyde (V) coupling of T₄ (I) to PLL (II).

C. The reaction is conducted in the presence of buffer of pH 9.5–10.

CASE 3: No intermediate remaining after reaction: 1-ethyl-3(3-dimethylaminopropyl)-carbodiimide (X) coupling of T₄ (IV) to PLL (V):

$$CH_3-CH_2-N=C=N-CH_2CH_2-N(CH_3)_2$$

(VII) 1-ethyl-3(3-dimethyl aminopropyl) carbodiimide (4)

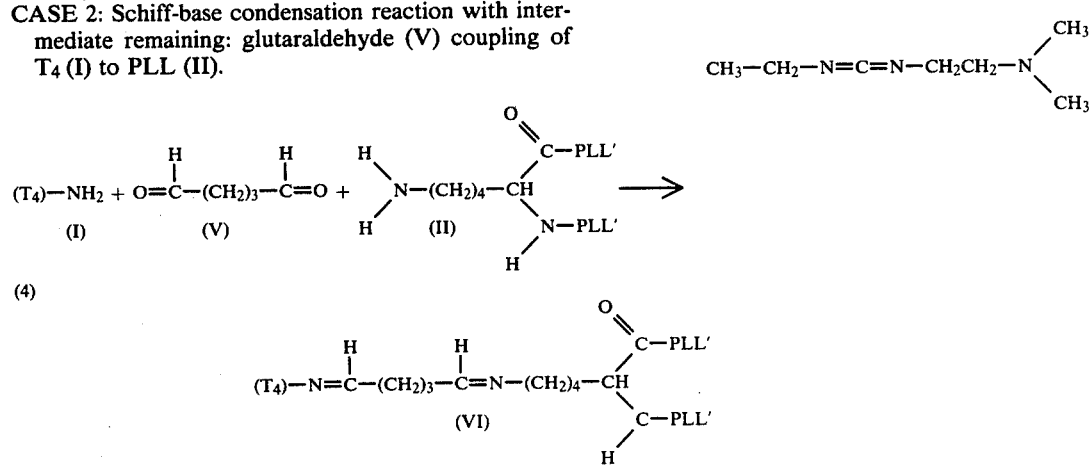

Here the glutaraldehyde molecule remains inserted as an intermediate even in the finished marker-spine material product. This reaction may be conducted from about −4° C. to about 40° C., and preferably about 23°

For this example T₄ (I) will be redrawn as

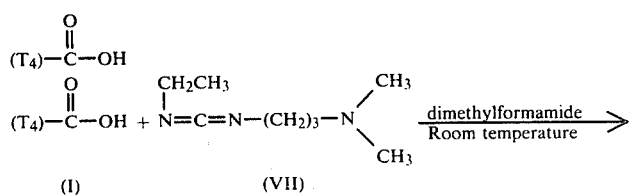

(5)

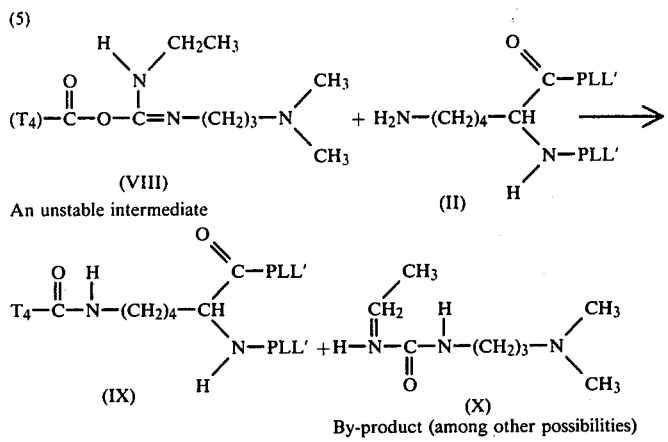

(VIII) An unstable intermediate (II)

(IX) T₄—PLL (X) By-product (among other possibilities)

As will be appreciated by those skilled in the art, it is the

OH group on the

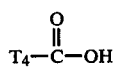

and the ε-amine group on the polylysine which react. This case is a preferable method of making a T₄-PLL intermediate compound, taking place at from 4° C. to about 40° C. in a dimethylformamide solvent and preferably at about room temperature (23°-28° C.) for a period of from 14-18 hours. Thyroxine is preferably employed in its free acid form, and polylysine in its hydrobromide form. After reaction, the product is purified starting materials (I) and (VII) and by-product (X) through a Sephadex G-25 column, manufactured by Pharmacia Fine Chemicals Incorporated of Piscataway, New Jersey. The "free acid" form of thyroxine is preferable because of its advantageous source of hydrogen ions.

solved in sodium hydroxide or ammonium hydroxide for initial dissolution.

CASE 4: EIA. Horseradish peroxidase as marker. No intermediate or coupling compound employed: addition of peroxidase to polymer-T₄ by Nakane oxidation (see P. K. Nakane and A. Kawaoi, *Journal of Histochemistry and Cytochemistry*, 22/12, 1084 (1974). If a

group occurs in a molecule (and it does in horseradish peroxidase) then treatment with sodium periodate will cause this reaction

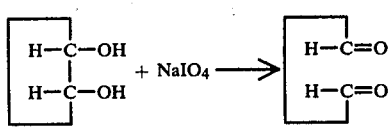

Addition of a free primary amine will cause a coupling to occur spontaneously forming a compound known as a Schiff base.

TABLE VI.
FORMS OF THYROXINE

| Form | Designation |
|---|---|
| (a) HO—⟨I,I⟩—O—⟨I,I⟩—CH₂—CH(NH₂)—C(=O)—OH | Free acid |
| (b) HO—⟨I,I⟩—O—⟨I,I⟩—CH₂—CH(NH₂)—C(=O)—O⁻Na⁺ · 5H₂O | Sodium salt pentahydrate |
| (c) HO—⟨I,I⟩—O—⟨I,I⟩—CH₂—CH(NH₂)—C(=O)—O⁻ NH₄⁺ | Ammonium salt |

If water is present, the second form of T₄ will function also in the reactions subsequent to the manufacture of our novel spine tool. In general T₄ is commonly dis-

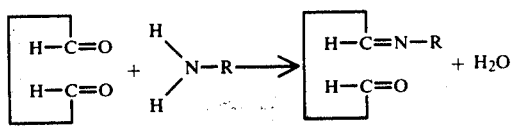

A reduction of the —C≡N— bond will make a stable compound.

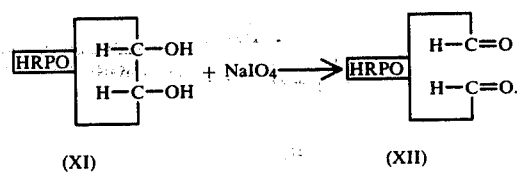

Schematic diagram of horseradish peroxidase molecule Using the latter compound:

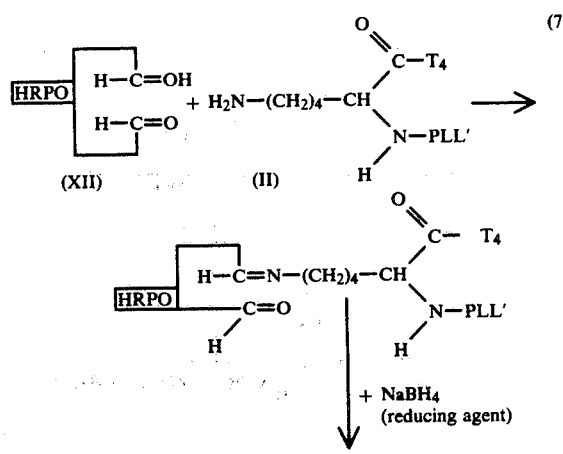

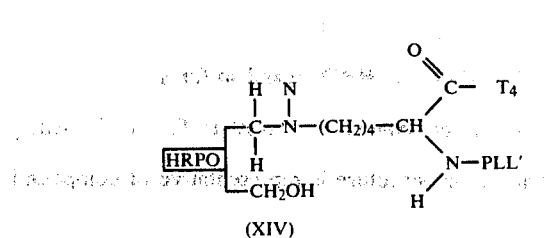

Reaction (5) may proceed from about 4° C. to about 40° C., and preferably at about 25° C., in the presence of a dimethylformamide-water solvent. See P. K. Nakane and A. Kawaoi, *Journal of Histochemistry and Cytochemistry*, 22/12, 1084 (1974).

Reaction (6) is conducted from about 4° C. to about 40° C., and preferably at about 25° C.

Methods and compounds suitable for coupling amino acids and proteins to be useful for chemical together are reviewed in J. H. Kennedy, L. J. Kricka, and P. Wilding, "Protein-protein Coupling Reactions and the Applications of Protein Conjugates", *Clinica Chimica Acta* 70, 1-31 (1976).

Preparation of diagnostic enzyme spine material products

As seen from cases 1-4 above, the procedure for the manufacture of enzyme marker material products may proceed by several different routes, depending on the intermediates (or "coupling compounds") employed or coupling chemistries involved. For example, TDIC (III) may be used with thyroxine in the following two-step reaction:

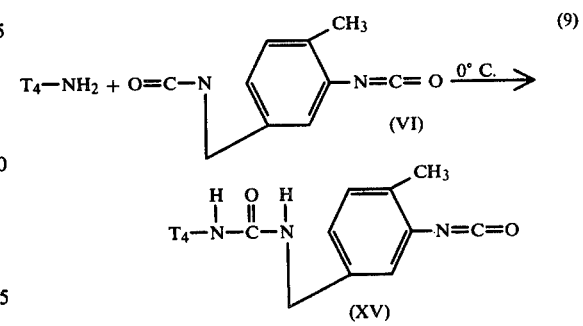

then react at a higher temperature with PLL:

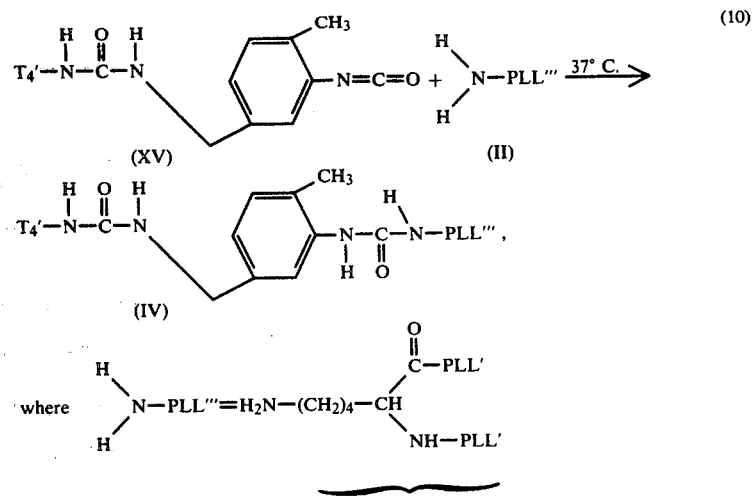

Alternatively, compound (IV) may be obtained in one step. Besides TDIC, carbodiimide coupling compounds may be also usually reacted in one or two-step process. Also, it is possible to employ the polymer (such as PLL, for example) first. There are a large number of coupling procedures known to those skilled in the art which may be used with the compounds to be coupled above. See J. H. Kennedy et al. cited above.

However as it is desired to limit the number of molecules of interest for the novel diagnostic marker spine tool to one, and as it is likewise desired to maximize the number of marker units on the spine product, in this case it is preferred to make the molecule of interest-polymer first the addition of the predetermined marker.

With the assumption that the molecule of interest-polymer is to be made first and the marker is to be added subsequently, the molecule of interest-polymer should be linked together by one or more covalent bonds, as may be appreciated by those skilled in the art. This covalent linking can be achieved either by direct condensation of existing side chains, or by addition of external bridging molecules. Many bivalent or polyvalent agents, bringing about coupling of protein molecules, have been reported in the literature and may be used to obtain conjugates as described above. (See. J. H. Kennedy et al., referred to previously.)

Preferable polymers are the homopolyamino acids, and a most preferable polymer is polylysine. A preferable enzyme is horseradish peroxidase.

In an especially preferred embodiment, the compound of interest is combined with the hydrogen bromide form of polylysine plus a molar excess of 1-ethyl-3(3-dimethylaminopropyl)carbodiimide (CDI) as intermediate (coupling compound) in dimethylformamide (DMF) solvent from about 23° C. to about 28° C., for from about 14 to about 18 hours, followed by purification on a Sephadex 6-25 column:

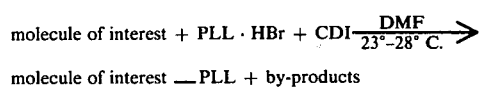
(11)

Then horseradish peroxidase (HRPO) is oxidized by NaIO₄ and after destruction of excess NaIO₄ per the method of Nakane and Kawaoi, is reacted with T₄-PLL intermediate forming a Schiff base intermediate. The oxidation reaction is allowed to terminate by the addition of an effective amount of ethylene glycol at 4° C. A small but effective amount of NaBH₄ may be added to reduce aldehyde groups of the Schiff base to alcohol (-OH) groups. The latter reaction sequence may be summarized as follows:

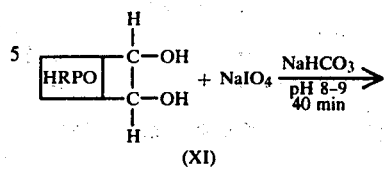
(XI)

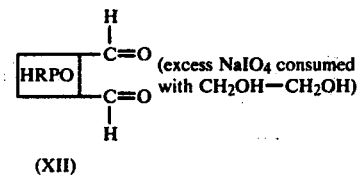
(XII)

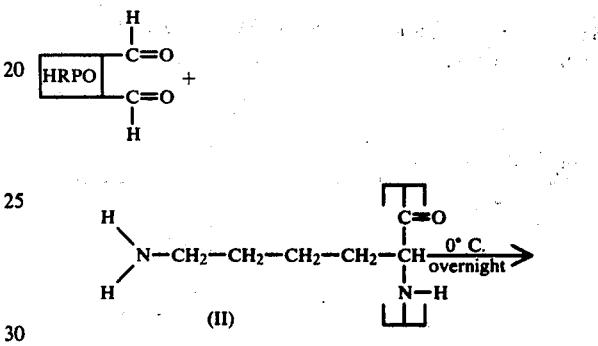

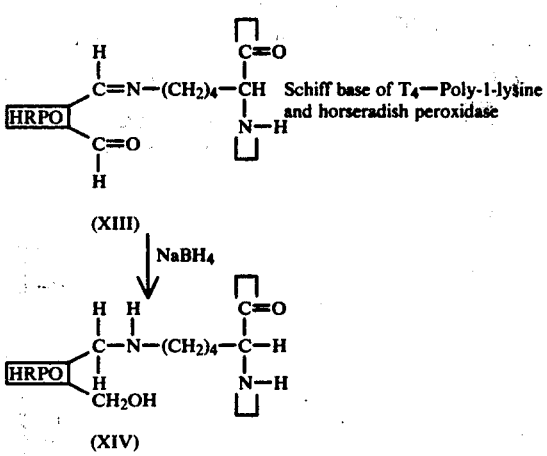
(XIII)
(XIV)

where compound (I-(B)) has the ultimate structure:

(X)₁-Poly-1-lysine(HRPO)ₙ where X is the compound of interest and includes:

X-Poly-1-lysine-(HRPO)₁

X-Poly-1-lysine-(HRPO)₂

X-Poly-1-lysine-(HRPO)₃

X-Poly-1-lysine-(HRPO)₄ and so forth.

Where the compound of interest is T₄, the following actual partial structure is representative of compound (I):

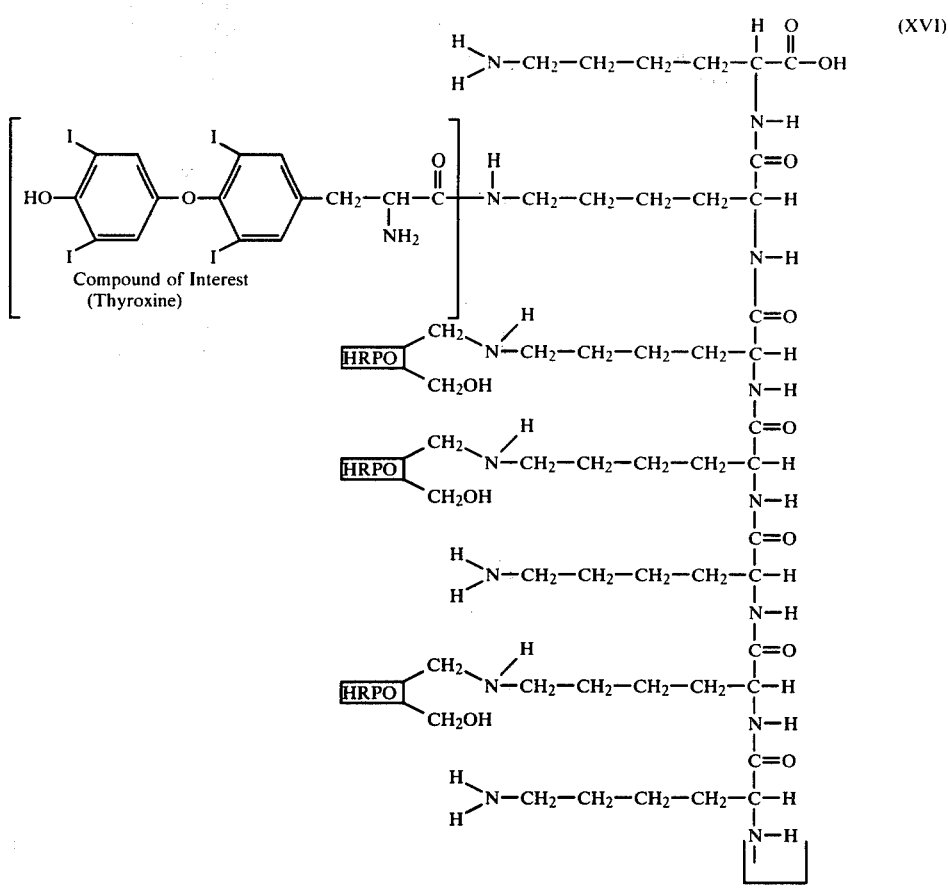

It has been found that the novel diagnostic marker spine tool described is not only convenient for use and capable of advance preparation, but is amazingly stable upon storage for extended periods. It is considered feasible to store such a tool for up to three or six months or more in inert atmosphere, e.g. under nitrogen, and in absence of moisture. It has been found also that low temperatures are not necessary for such stability, as temperatures such as 25° C., and 37° C., have been found suitable for storage. Thus by vacuum packing, hermetic sealing etc. it is feasible to ship the tool of the present invention in unrefrigerated packages, and retain effectiveness despite possible long delays in transit etc. As a precaution it may be desirable to keep the tool refrigerated, possibly near the freezing point or about 4° C., but the ordinary temperature stability will still be advantageous because of possible exposure to such temperatures prior to use or the economic advantage of being able to ship without refrigeration.

3. Use of the Diagnostic Marker Spine Product

Once the novel diagnostic marker spine tool of my invention is manufactured, isolated in substantially pure form, and combined with the molecule of interest it can be utilized in the same fashion as the similar labeled molecule of interest (antigen, antibody, hapten, protein or other molecule of interest currently employed in the art.

For example, if an enzyme marker is chosen, after combining with the molecule of interest, the novel diagnostic enzyme spine tool can be utilized (1) in the same fashion as the corresponding enzyme-linked protein, antibody, antigen, etc., is employed in U.S Pat. Nos. 3,654,090; 3,791,932; 3,839,153; 3,850,752; 3,879,262; 4,016,043; and U.S. Reissue Patent No. 29,169 (incorporated herein by reference) if an insoluble phase is employed, or (2) in the same fashion as enzyme-linked protein, antibody, antigen, or other molecule of interest as taught in U.S. Pat. Nos. 3,880,715; 3,852,157; 3,875,011; 3,935,074; and 3,905,871 and an article by Kenneth S. Rubenstein et al in "Homogenous" Enzyme immunoassay, a New Immunochemical Technique", Biochemical and Biophysical Research Communications, 47, No. 4, 846–851 (1972) (all incorporated herein by reference) if an insolubilized phase is not employed and the assay depends on inhibition or activation of the enzyme label by antibody binding.

For example, if an enzyme marker is chosen and a preference is made to use an insolubilized phase in the reaction scheme, one may use the novel diagnostic enzyme spine tool in a simple "competitive" method as taught in U.S. Pat. No. 3,654,090, or in a "sandwich" method as taught in U.S. Pat. No. 4,016,043 for example, or in a "DASP" method as taught in U.S. Pat. No. 3,839,153. As taught above, if a specified enzyme having a fixed rate of conversion of the substrate and a high purity is employed for a specific method of EIA, the specific activity will be proportional to the degree of incorporation of enzyme molecules in each molecule of labeled substance, and the method will become more effective. Hence, the more enzyme molecules/molecule of labeled substance, the higher the specific enzymatic activity. Thus the present invention gives a way of chemically coupling several enzyme molecules to a substance to be labeled such that the enzymatic specific activity of the labeled substance will be raised dramatically.

The instantly claimed invention can be used for reagents and in conventional test kits, for example those test kits also set forth in detail in U.S. Pat. Nos. 3,654,090; 3,850,752; 3,838,153; 3,879,262; and 4,016,043. The term "kit" is employed herein to mean a collection of all or some of the chemicals, including the assay tubes, and instructions necessary to do a marker assay.

General operating aspects of the invention have been disclosed herein but the invention should not be restricted by the disclosures herein but only by reference to the herein appended claims.

The following are examples of specific diagnostic spine tools and their methods of manufacture according to the invention. As indicated above, however, a wide variety of specific spine tools are within the scope of the invention and may be made by a variety of methods according to the invention, so that the following examples must be deemed as being representative of the present invention.

EXAMPLE 1

This example shows the formation of a new diagnostic marker spine tool of thyroxine (Calbiochem Incorporated, LaJolla, Cal.) poly-1-lysine (PLL) and horseradish peroxidase (HPRG).

Thyroxine in its free acid form in an amount of 81.3 mg (Calbiochem lot 601419), 228 mg of poly-1-lysine HBr (Sigma lot 95C-5039 of the Sigma Corporation of St Louis, Mo.) and 228.8 mg of 1-ethyl-3-(3-dimethylaminopropyl) carbodiimide (CDI, as intermediate) were placed in 10 ml of dimethylformamide (DMF - a solvent) at a temperature of from about 23° to about 28° C. and mixed and reacted for a period of about 14 to 18 hours, and then purified using a Sephadex G-25 column (made by Pharmacia Fine Chemicals, Inc., of Piscataway, N.J.). 35.5 mg (0.89 $\mu$moles) of horseradish peroxidase was mixed and reacted in a 15 ml polypropylene tube with 5 ml of a 1 molar solution of $NaHCO_3$ (a buffer) and the purified $T_4$-PLL product above with about 720 mg (3.4 millimoles) of $NaIO_4$ to oxidize cis hydroxyl groups to corresponding aldehyde groups. The oxidation reaction was terminated by the addition of ethylene glycol. The ethylene glycol is employed to quench the oxidation reaction by a total consumption of the sodium metaperiodate.

Thereafter, about $6.06 \times 10^{-4}$ millimoles of $T_4$-poly-1-lysine was added and the Schiff base formation was continued overnight at 4° C. The next morning about 300 mg of $NaBH_4$ was added to effect reduction of the Schiff base to the aliphatic groups and reduce primary aldehydes to hydroxyl group. Purification by exclusion chromatography on Sephadex G-25 and characterization followed.

EXAMPLE 2

The sodium salt of thyroxine ($T_4$) (lot 600353 of the Calbiochem Company, LaJolla, Calif.) instead of the free $T_4$ of Example 1 was added in an amount of 81.3 mg to 10 ml of dimethylformamide (DMF - a solvent). Thereafter 228.8 mg 1-ethyl-3(3-dimethylaminopropyl) carbodiimide (CDI, obtained from Calbiochem, lot 601419) in 2 ml of water was added to the $T_4$, dropwise with stirring, followed by the addition of 288 ml of poly-1-lysine HBr (Sigma lot 95C-5039 of the Sigma Corporation of St. Louis, Mo.) dissolved in 10 ml of DMF followed by refrigeration of the mixture at 10° C. overnight. The Sigma lot 95C-5039 poly-1-lysine may be further characterized as having 16 lysine residues per molecule and approximately 3400 g/mole molecular weight. After refrigeration overnight, the pH of the solution was adjusted to 8.3 with sodium hydroxide after one hour of reaction had taken place. The resulting precipitate which had formed overnight was dissolved by adding 6 N HCl, and the reaction mixture was added to a 20 cm high $\times$ 2.5 cm diameter column containing Sephadex G-25 (Pharmacia Fine Chemicals). Water was used for elution of the fractions initially and 7 ml aliquots were collected. A band of brown color remained at the top of the column and DMF was used to collect additional fractions. It was determined by ultraviolet spectrometer that the DMF fractions contained $T_4$-poly-1-lysine. These fractions of $T_4$-PLL product were concentrated, taken up in 7 ml DMF, and stored as a liquid in a freezer at $-20°$ C.

Then 35.5 g of horseradish peroxidase (Sigma lot No. 26C-5005-1, Fraction VI) was dissolved in 3 ml of $NaHCO_3$ at a pH of 9.1. Thereafter, saturated $NaIO_4$ in water (5.0 ml) was added, followed by adjustment of the pH with sodium hydroxide to 8.5. Oxidation was allowed to proceed for 40 minutes, at which time 5 ml of 0.1 M ethylene glycol was added to stop the oxidation. Then 0.1 ml of $T_4$-PLL in DMF was added and the Schiff base formation was allowed to proceed overnight at refrigeration temperatures (about 10° C.). The next morning 0.1 g $NaBH_4$ was added to reduce the Schiff base, followed by fractionation of the product on a column packed with Sephadex G-150, manufactured by the Pharmacia Corporation. The G150 column uses a dextran whose molecular purification range is from about 5000 g/mole to about 400,000 g/mole. The collected fractions, each in an amount of 2.5 ml, were tested for enzyme activity, using 2.0 ml of a color development solution containing 10 mg urea peroxidase and 35 mg ortho-phenylenediamine as the substrate and reducing agent respectively per 50 ml of 0.033 molar citric acid and 0.066 molar $Na_2HPO_4$ at pH 5.0. The color reaction was terminated with 1.0 ml 1 molar citric acid. The color, an orange-yellow, was measured on a spectrophotometer at 492 nm wavelength: intense at fractions 2-5, much less intense at fractions 7-8, and faint at fractions 11-15, showing the presence of horseradish peroxidase incorporated multiply in the several groups of fractions.

The fractions collected above were also tested using a system containing polystyrene beads with anti-thyroxine gamma globulin adsorbed thereto. After incubation with aliquots of the $T_4$-PLL-$(HRPO)_p$ fractions, the beads were rinsed such that any enzyme not attached to $T_4$ was removed and the enzyme activity shown again with color development solution. Again, three bands of color were found matching the initially found fractions. Since $T_4$ was removed by the Sephadex G-25 liquid chromatography from the $T_4$-PLL before a reaction with the horseradish peroxidase, the antibody-bound enzyme activity was from forms of $T_4$-PLL-$(HRPO)_p$ only.

While presently preferred embodiments of the invention have been given for the purpose of disclosure, obvious changes known to those skilled in the art may be made which are within the spirit of the invention as defined by the appended claims.

What I claim as my invention is:

1. A reagent for the determination of a component of the antigen-antibody reaction comprising
   (1) an antigen or antibody and
   (2) the other component covalently linked to an enzyme-spine material product having the formula

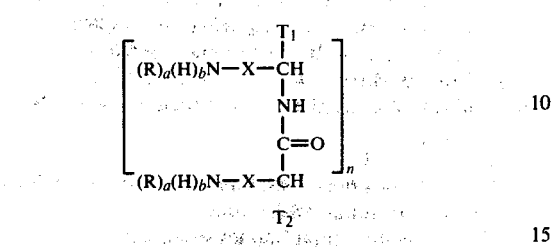

wherein R is an organic group labeled with a radioisotope, fluorescent group, lysis-initiating compound, enzyme or other suitable marker material and depending on the coupling chemistry selected, linking moieties;

$T_1$ and $T_2$ are individually selected from the group consisting of —CH$_3$,

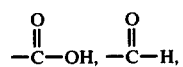

—CH$_2$OH, —CH$_2$SH and —NH$_2$;

X is selected from the group consisting of a divalent group of the formula (CH$_2$)$_m$ wherein m is an integer from 0 to about 10, phenylene, halogen-substituted phenylene, alkyl substituted phenylene, or aminated phenylene group;

a is 0, 1 or 2;

b is 2-a, with the proviso that there be at least two R groups in the product; and n is a number of from one to about 100,000.

2. The reagent of claim 1 wherein the marker material is the enzyme peroxidase.

3. The reagent of claim 2 wherein said peroxidase is horseradish peroxidase.

4. A reagent for the determination of a hapten being a protein-free substance that is not capable of stimulating antibody formation but which reacts with antibodies by means of a binding protein capable of reacting to bind said hapten specifically, comprising:
   (1) the coupling product of said hapten and an enzymespine material product having the formula

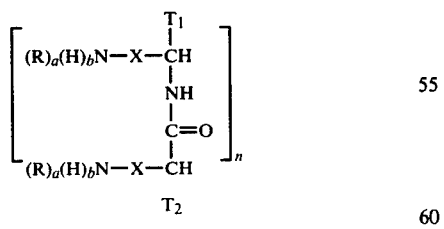

where R is a group containing a radioisotope, fluorescent material, lysis-initiating compound, spine, or other suitable marker material lacking in linking atom and depending on the coupling chemistry selected, a linking moiety;

$T_1$ and $T_2$ are individually selected from the group consisting of —CH$_3$,

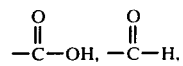

—CH$_2$OH, —CH$_2$SH, and —NH$_2$;

X is selected from the group consisting of a divalent unit of the formula (CH$_2$)$_m$ wherein m is an integer from 0 to about 10, phenylene, hydroxyl-substituted phenylene, halogen-substituted phenylene, alkyl substituted phenylene, and aminated phenylene groups;

a is 0, 1, or 2;

b is 2-a, with the proviso that there be at least two R groups in the product; and n is a number of from one to about 100,000; and (2) a binding protein capable of reacting to bind said hapten and said hapten-marker-spine material coupling product.

5. A reagent for the determination of a component of an antigenantibody reaction selected from the group consisting of an antigen and an antibody, comprising:
   (1) one of said components coupled to a carrier,
   (2) a substance having the same immunological properties as the component in (1) covalently linked to an enzyme-spine material product having the formula

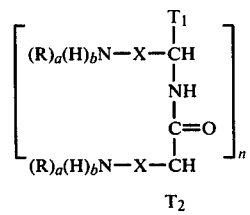

wherein R is an organic group labeled with a radioisotope, fluorescent material, lysis initiating material, enzyme, or other suitable marker material lacking a linking atom; and depending on the coupling chemistry selected, a linking moiety;

$T_1$ and $T_2$ are individually selected from the group consisting of

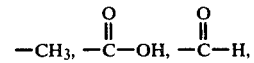

—CH$_2$OH, —CH$_2$SH, and —NH$_2$;

X is selected from the group consisting of a divalent unit of the formula (CH$_2$)$_m$ wherein m is an integer from 0 to about 10, phenylene, hydroxyl-substituted phenylene, halogen-substituted phenylene, alkyl substituted phenylene, or aminated phenylene groups;

a is 0, 1, or 2;

b is 2-a, with the proviso that there be at least two R groups in the product; and n is a number from one to about 100,000; and (3) the binding partner of the component to be determined if the component to be determined has the same immunological properties as the component in (1).

6. The reagent of claim 5, wherein said carrier is a water-spine insoluble, water-insusceptible, solid carrier.

7. A diagnostic tool for immunoassay comprising a marked-spine material product of the formula

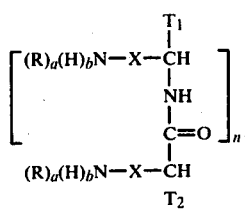

wherein R is an organic group labeled with a radioisotope, fluorescent group, lysis-initiating compound, enzyme or other suitable marker material lacking a linking atom;

$T_1$ and $T_2$ are individually selected from the group consisting of —$CH_3$,

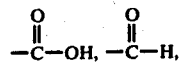

—$CH_2OH$, —$CH_2SH$, and —$NH_2$;

X is selected from the group consisting of a divalent group of the formula $(CH_2)_m$ wherein m is an integer from 0 to about 10, phenylene, hydroxyl-substituted phenylene, halogen-substituted phenylene, alkyl substituted phenylene or aminated phenylene group;

a is 0, 1, or 2;

b is 2-a, with the proviso that there be at least one R group in the product; and n is a number from 1 to about 100,000.